(12) United States Patent
Nikittin et al.

(10) Patent No.: US 11,573,174 B2
(45) Date of Patent: Feb. 7, 2023

(54) OPTICAL GAS CONCENTRATION MEASUREMENT APPARATUS

(71) Applicant: Advanced Energy Industries, Inc., Fort Collins, CO (US)

(72) Inventors: Alex S. Nikittin, San Jose, CA (US); Stefan Warnke, Scotts Valley, CA (US); Eric Wertz, Oakland, CA (US)

(73) Assignee: Advanced Energy Industries, Inc., Denver, CO (US)

( * ) Notice: Subject to any disclaimer, the term of this patent is extended or adjusted under 35 U.S.C. 154(b) by 0 days.

(21) Appl. No.: 17/156,955

(22) Filed: Jan. 25, 2021

(65) Prior Publication Data

US 2022/0236173 A1   Jul. 28, 2022

(51) Int. Cl.
*G01J 5/00*      (2022.01)
*G01N 21/3504*   (2014.01)
*G01N 33/00*     (2006.01)

(52) U.S. Cl.
CPC ..... *G01N 21/3504* (2013.01); *G01N 33/0027* (2013.01); *G01N 2201/0633* (2013.01); *G01N 2201/0636* (2013.01); *G01N 2201/0638* (2013.01)

(58) Field of Classification Search
CPC .......... G01N 21/3504; G01N 33/0027; G01N 2201/0633; G01N 2201/0636; G01N 2201/0638
See application file for complete search history.

(56) References Cited

U.S. PATENT DOCUMENTS

| 9,651,488 B2 | 5/2017 | Scherer et al. | |
| 2012/0120397 A1* | 5/2012 | Furtaw | G01N 21/3504 356/246 |
| 2012/0287418 A1* | 11/2012 | Scherer | G01N 33/004 356/51 |
| 2015/0247788 A1* | 9/2015 | Paul | G01N 21/31 356/338 |
| 2016/0377533 A1* | 12/2016 | Kusaba | G01N 33/497 250/339.13 |

OTHER PUBLICATIONS

Anton et al., "Improvements in NDIR Gas Detection Within the Same Optical Chamber", "Proceedings of SPIE—The International Society for opetical Engineering", Sep. 2011, pp. 7, Publisher: Retrieved from https://www.researchgate.net/publication/238527523.

* cited by examiner

*Primary Examiner* — Kiho Kim
(74) *Attorney, Agent, or Firm* — Neugeboren O'Dowd PC

(57) ABSTRACT

An optical gas concentration measurement apparatus is disclosed. The optical gas concentration measurement apparatus includes a thermally insulated enclosure that has a gas sample cell situated within. A thermally-insulating, light-guiding element passes through an access port of the thermally insulated enclosure and is configured to direct light from a light source outside of the thermally insulated enclosure to the gas sample cell. A light detector outside of the thermally insulated enclosure is optically coupled to the gas sample cell and an electronic assembly outside of the thermally insulated enclosure is configured to receive information from the light detector.

6 Claims, 6 Drawing Sheets

OPTICAL GAS CONCENTRATION MEASUREMENT APPARATUS

FIELD OF THE DISCLOSURE

The present disclosure relates generally to gas concentration measurement devices. In particular, but not by way of limitation, the present disclosure relates to optical gas concentration measurement devices.

BACKGROUND

Currently, many chemical processes, such as chemical vapor deposition (CVD) processes, require exact gas concentration monitoring in a controlled high temperature chamber. Some of these chemical processes utilize optical gas concentration measurement sensors, such as nondispersive infrared (NDIR) gas concentration sensors, to monitor gas concentration. A typical NDIR gas concentration sensor includes a gas sample cell, an infrared (IR) light source, an IR detector, and an electronic assembly that receives information from the IR detector. The IR light source emits light through the gas sample cell and to the IR detector, and the amount of light transmitted from the IR light source to the IR detector can be used to infer a concentration of a gas within the gas sample cell. In some cases, gas temperature and pressure sensors are included in the NDIR gas concentration sensor and may send gas temperature and pressure measurements from the gas sample cell to the electronic assembly where gas temperature, gas pressure, and IR detector measurements can be used to infer the gas concentration within the gas sample cell.

However, high temperature environments, such as those found in many CVD processes, may significantly limit the lifetime of such NDIR gas concentration sensors, as well as many other types of gas sensor, since many of the electronic components experience dramatically shortened lifetimes when exposed to high temperatures, such as temperatures in excess of 100° C. Additionally, many gas sample cells of NDIR gas concentration sensors utilize reflective walls to aid in the propagation of light from the IR light source to the IR detector; however, such reflective walls lose reflectance over time due to contamination caused by the gas within the gas sample cell. This reflectance loss significantly impairs the performance of the NDIR gas concentration sensor, especially as the reflectance losses become multiplicative with multiple reflections.

There is therefore a need in the art for a new optical gas concentration measurement apparatus that addresses some of the current shortcomings, particularly those involved in measuring gas concentrations in high temperature environments and those related to reduced performance due to gas sample cell wall contamination.

SUMMARY

The following presents a simplified summary relating to one or more aspects disclosed herein. As such, the following summary should not be considered an extensive overview relating to all contemplated aspects, nor should the following summary be regarded to identify key or critical elements relating to all contemplated aspects and/or embodiments or to delineate the scope associated with any particular aspect. Accordingly, the following summary has the sole purpose to present certain concepts relating to one or more aspects relating to the mechanisms disclosed herein in a simplified form to precede the detailed description presented below.

Some aspects of the present disclosure may be characterized as an optical gas concentration measurement apparatus comprising a thermally insulated enclosure having one or more access ports and a gas sample cell situated within the thermally insulated enclosure, the gas sample cell comprising one or more optical windows and one or more gas flow ports. The optical gas concentration measurement apparatus may include a light source outside of the thermally insulated enclosure configured to provide light to the gas sample cell and a first thermally-insulating, light-guiding element passing through a first access port of the thermally insulated enclosure, the first thermally-insulating, light-guiding element configured to direct light from the light source to the gas sample cell via the one or more optical windows. The optical gas concentration measurement apparatus may include a light detector outside of the thermally insulated enclosure configured to receive light from the gas sample cell via the one or more optical windows and an electronic assembly outside of the thermally insulated enclosure configured to receive information from the light detector.

Other aspects of the present disclosure may be characterized as an optical gas concentration measurement apparatus that comprises a thermally insulated enclosure having one or more access ports and a gas sample cell situated within the thermally insulated enclosure, the gas sample cell configured to have a first optical window and a second optical window on two opposing ends and to have one or more gas flow ports. The optical gas concentration measurement apparatus may include a light source thermally isolated from and positioned outside of the thermally insulated enclosure, the light source configured to provide light to the gas sample cell, and a first thermally-insulating light guide configured to direct light from the light source to the gas sample cell with a first end adjacent to the light source and a second end adjacent to the first optical window of the gas sample cell and with a body of the first thermally-insulating light guide passing through a first access port of the thermally insulated enclosure. The optical gas concentration measurement apparatus may include a reflective element positioned within the thermally insulated enclosure and adjacent to the second optical window of the gas sample cell, the reflective element configured to reflect light from the first thermally-insulating light guide towards the first optical window. The optical gas concentration measurement apparatus may include a light detector thermally isolated from and positioned outside of the thermally insulated enclosure, the light detector configured to receive light from the gas sample cell via the first optical window, and an electronic assembly thermally isolated from and positioned outside of the thermally insulated enclosure, the electronic assembly configured to receive information from the light detector.

Other aspects of the present disclosure may be characterized as an optical gas concentration measurement apparatus that comprises a thermally insulated enclosure having one or more access ports and a gas sample cell situated within the thermally insulated enclosure, the gas sample cell comprising one or more optical windows and one or more gas flow ports. The optical gas concentration measurement apparatus may include a light source outside of the thermally insulated enclosure configured to provide light to the gas sample cell and a means for directing light from the light source to the gas sample cell via the one or more optical windows while thermally insulating the light source from the gas sample cell. The optical gas concentration measurement apparatus may include a light detector outside of the thermally insulated enclosure configured to receive light from the gas sample cell and provide information indicative of a chemistry within the gas sample cell. The optical gas concentration measurement apparatus may include a means for receiving the light from the gas sample cell via the one or more optical windows and conveying the light to the light detector while thermally insulating the light detector from the gas sample cell. The optical gas concentration measurement apparatus may include an electronic assembly outside of the thermally insulated enclosure configured to receive the information indicative of a chemistry from the light detector and provide a user-readable output to convey the information to an operator of the measurement apparatus.

DETAILED DESCRIPTION

Figure 1:
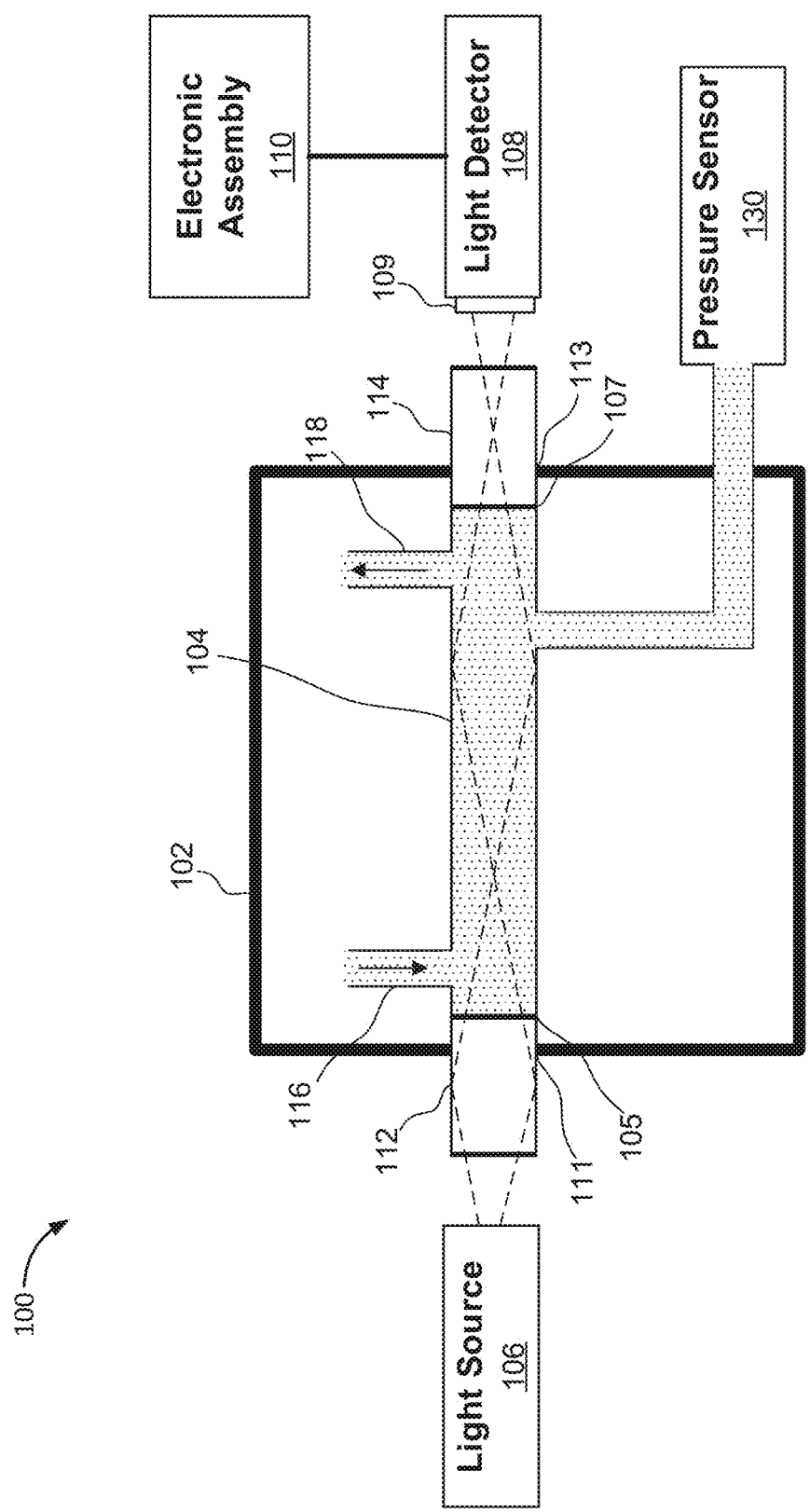
FIG. 1 illustrates a block diagram of an exemplary optical gas concentration measurement apparatus with a single-pass optical configuration, in accordance with one or more embodiments.

The word "exemplary" is used herein to mean "serving as an example, instance, or illustration." Any embodiment described herein as "exemplary" is not necessarily to be construed as preferred or advantageous over other embodiments.

The present disclosure may enable an increased lifetime of optical gas concentration measurement apparatuses by limiting the thermal exposure of temperature-sensitive components, such as electronic components, to high temperature environments. The present disclosure may also enable more precise control of a chemical process gas temperature by providing thermal isolation for heat-producing components of an optical gas concentration measurement apparatus preventing the transfer of heat from such components to the chemical process gas. The present disclosure may also enable a superior long-term level of performance of optical gas concentration measurement apparatuses by reducing the impact of gas sample cell wall contamination on light transmitted through the gas sample cell.

Some embodiments of the present disclosure may comprise an optical gas concentration measurement apparatus with a thermally insulated enclosure having one or more access ports. A gas sample cell may be situated within the thermally insulated enclosure and may have one or more optical windows and one or more gas flow ports. The gas sample cell may be configured to receive a gas through the one or more gas flow ports. For example, the gas may be a chemical process gas at a high temperature, such as 100° C. or more, but low pressure and concentration. A light source, a light detector, and an electronic assembly may be positioned outside of the thermally insulated enclosure. The light source may be configured to provide light to the gas sample cell, and the light detector may be configured to receive light from the gas sample cell via the one or more optical windows. The electronic assembly may be configured to receive information from the light detector, such as information relating to the amount of light received by the light detector. The electronic assembly may be configured to infer a concentration of the gas received by the gas sample cell based on the information received from the light detector. One or more thermally-insulating optical elements may pass through the one or more access ports of the thermally insulated enclosure and be configured to transmit light from the light source to the light detector. Examples of thermally-insulating optical elements may include thermally-insulating light pipes, light guides, optical fibers, or a system of coupled relay lenses, wherein each thermally-insulating optical element is a single unitary part.

For example, the thermally-insulating optical elements may be realized, in some embodiments, by a tube constructed of thermally-insulating materials with a window on each end that allows light to pass from the light source to the light detector via the gas sample cell. The thermally-insulating optical elements and thermally insulated enclosure may be configured to provide enough thermal insulation so as to thermally isolate the gas sample cell from the components of the optical gas concentration measurement apparatus positioned outside of the thermally insulated enclosure, which may enable an increased lifetime of the optical gas concentration measurement apparatus by limiting the exposure of such components to high temperatures. The thermal isolation provided by the thermally insulated enclosure and thermally-insulating optical elements may also prevent the transfer of heat from the components of the optical gas concentration measurement apparatus to the gas sample cell and any gas received by the gas sample cell, enabling more precise temperature control of gases received by the gas sample cell.

In some embodiments, the thermally-insulating optical elements may be thermally-insulating, light-guiding elements configured to direct, or guide, light from the light source to the gas sample cell via the one or more optical windows. For example, the light source may emit uncollimated light, and a first thermally-insulating, light-guiding element passing through a first access port of the thermally insulated enclosure and may collimate the light from the light source, such as through utilizing a tapered cylindrical shape, directing the light away from the walls of the gas sample cell and along a more direct path towards the light detector. The directing of light by the thermally-insulating, light-guiding elements away from the gas sample cell walls may reduce the impact of gas sample cell wall contamination on light transmission through the gas sample cell, enabling superior long-term performance of the optical gas concentration measurement apparatus.

In some embodiments, the thermally-insulating, light-guiding elements may be configured to direct light from gas sample cell to the light detector. For example, light may pass out of the gas sample cell through the one or more optical windows and be directed towards the light detector by a second thermally-insulating, light guiding element, which may have a tapered cylindrical, a tapered rectangular prism, or a tapered square prism shape and may pass through a second access port of the thermally insulated enclosure. The directing of light by the thermally-insulating, light-guiding elements towards the light detector may enable a more sensitive and accurate gas concentration measurement with a greater proportion of light transmitted through the gas sample cell being directed to and received by the light detector.

In some embodiments, one or more reflective elements may be positioned within the thermally insulated enclosure adjacent to one or more of the optical windows of the gas sample cell. The reflective elements may be configured to reflect light from the light source to the light detector via the gas sample cell. Such reflective elements may enable optical access to the gas sample cell for the light source and light detector via a fewer access ports of the thermally insulated enclosure, which may be advantageous in applications with space constraints, and may enable multiple-pass configurations of the light through the gas sample cell, which may aid in accurately detecting low concentration gasses.

Referring now to the drawings, FIG. 1 illustrates a block diagram of an exemplary optical gas concentration measurement apparatus 100 with a single-pass optical configuration. The optical gas concentration measurement apparatus 100 may comprise a thermally insulated enclosure 102 having one or more access ports, which may include a first access port 111 and a second access port 113 on opposing sides of the thermally insulated enclosure. A gas sample cell 104 may be situated within the thermally insulated enclosure 102 and may have one or more optical windows, which may include a first optical window 105 proximate the first access port 111 and a second optical window 107 proximate the second access port 113, and one or more gas flow ports, which may include an inlet gas flow port 116 and an outlet gas flow port 118. The gas sample cell 104 may be configured to receive a gas, such as a high temperature chemical process gas, through the inlet gas flow port 116 and expel the gas through the outlet gas flow port 118. A light source 106, a light detector 108, an electronic assembly 110, and a pressure sensor 130 may be positioned outside of the thermally insulated enclosure 102. The light source 106 may be configured to provide light to the gas sample cell 104 via the first optical window 105, and the light detector 108 may be configured to receive light from the gas sample cell 104 via the second optical window 107. The electronic assembly 110 may be configured to receive information from the light detector 108, such as information relating to the amount of light received by the light detector 108. The pressure sensor 130 may be connected to the gas sample cell 104 so that the pressure sensor 130 may sample and measure the pressure of the environment within the gas sample cell 104 and send a resulting pressure measurement to the electronic assembly 110. The electronic assembly 110 may be configured to infer a concentration of the gas received by the gas sample cell 104 based on the information received from the light detector 108 and the pressure measurement from the pressure sensor 130.

A first thermally-insulating optical element 112 may pass through the first access port 111 of the insulated enclosure 102 proximate the first optical window 105 and be configured to transmit light from the light source 106 to the gas sample cell 104 via the first optical window 105. A second thermally-insulating optical element 114 may pass through the second access port 113 of the insulated enclosure 102 proximate the second optical window 107 and be configured to transmit light from the gas sample cell 104 to the light detector 108 via the second optical window 107. The first thermally-insulating optical element 112 and second thermally-insulating optical element 114 may each be realized, for example, by a tube with reflective internal walls, which may aid in light transmission, that may be constructed of one or more thermally-insulating materials and have a window on each end enabling light transmission into and out of the tube; however, it is contemplated that other thermally-insulating optical elements that form a single unitary part, such as those comprising light pipes, light guides, optical fibers, or systems of coupled relay lenses, may be utilized without departing from the scope or spirit of the present application.

The first thermally-insulating optical element 112, the second thermally-insulating optical element 114, and the thermally insulated enclosure 102 may be configured to provide enough thermal insulation so as to thermally isolate the gas sample cell 104 from the components of the optical gas concentration measurement apparatus 100 positioned outside of the thermally insulated enclosure 102, which may enable an increased lifetime of the optical gas concentration measurement apparatus 100 by limiting the exposure of such components to high temperatures. The thermal isolation provided by the first thermally-insulating optical element 112, the second thermally-insulating optical element 114, and the thermally insulated enclosure 102 may also prevent the transfer of heat from the components of the optical gas concentration measurement apparatus 100 positioned outside of the thermally insulated enclosure 102 to the gas sample cell 104 and any gas received by the gas sample cell 104, enabling more precise temperature control of gases received by the gas sample cell 104.

The light source 106 may be configured to provide broad-spectrum, uncollimated light to the gas sample cell 104. For example, the light source 106 may be an IR light source that emits uncollimated, broad-spectrum IR light. The light from the light source 106 may pass through the first thermally-insulating optical element 112 and into the gas sample cell 104 via the first optical window 105. As the light passes through the gas sample cell 104, the gas received by the gas sample cell 104 may absorb a portion of the light. The light may then pass through the second thermally-insulating optical element 114 via the second optical window 107 and into the light detector 108. An optical filter 109 may be coupled to the light detector 108 and be configured to filter the light passing into the light detector 108 from the gas sample cell 104, enabling the light detector 108 to be tuned to detect specific gases. For example, the optical filter 109 may be a band-pass filter tuned to allow a specific wavelength of light associated with a specific gas to pass through to the light detector 108. The light detector 108 may emit a signal to the electronic assembly 110 based on the amount of light detected. The internal walls of the gas sample cell 104, the first thermally-insulating optical element 112, and the second thermally-insulating optical element 114 may be reflective to aid in the propagation of uncollimated light from the light source 106 to the light detector 108, as shown by the exemplary light rays represented by dotted lines in the figure.

In other embodiments, the light source 106 may provide broad-spectrum, collimated light to the gas sample cell 104. The broad-spectrum, collimated light may follow a similar path as the broad-spectrum, uncollimated light mentioned above; however, the broad-spectrum, collimated light may be focused so that minimal wall interaction occurs. This reduced wall interaction may enable the gas sample cell 104, the first thermally-insulating optical element 112, and the second thermally-insulating optical element 114 to transmit similar amounts of light to the light detector 108 without the use of reflective internal walls as in some broad-spectrum, uncollimated light embodiments.

In other embodiments, the light source 106 may be a laser that follows a similar path to the broad-spectrum collimated light mentioned above. The wavelength of the laser may be chosen based on the type of gas to be detected. In embodiments featuring a laser as the light source 106, the optical filter 109 may optionally be removed since the laser light may not need filtering. However, using only a specific wavelength of light may limit the number of different gas types that can be detected by the light detector 108.

Figure 2:
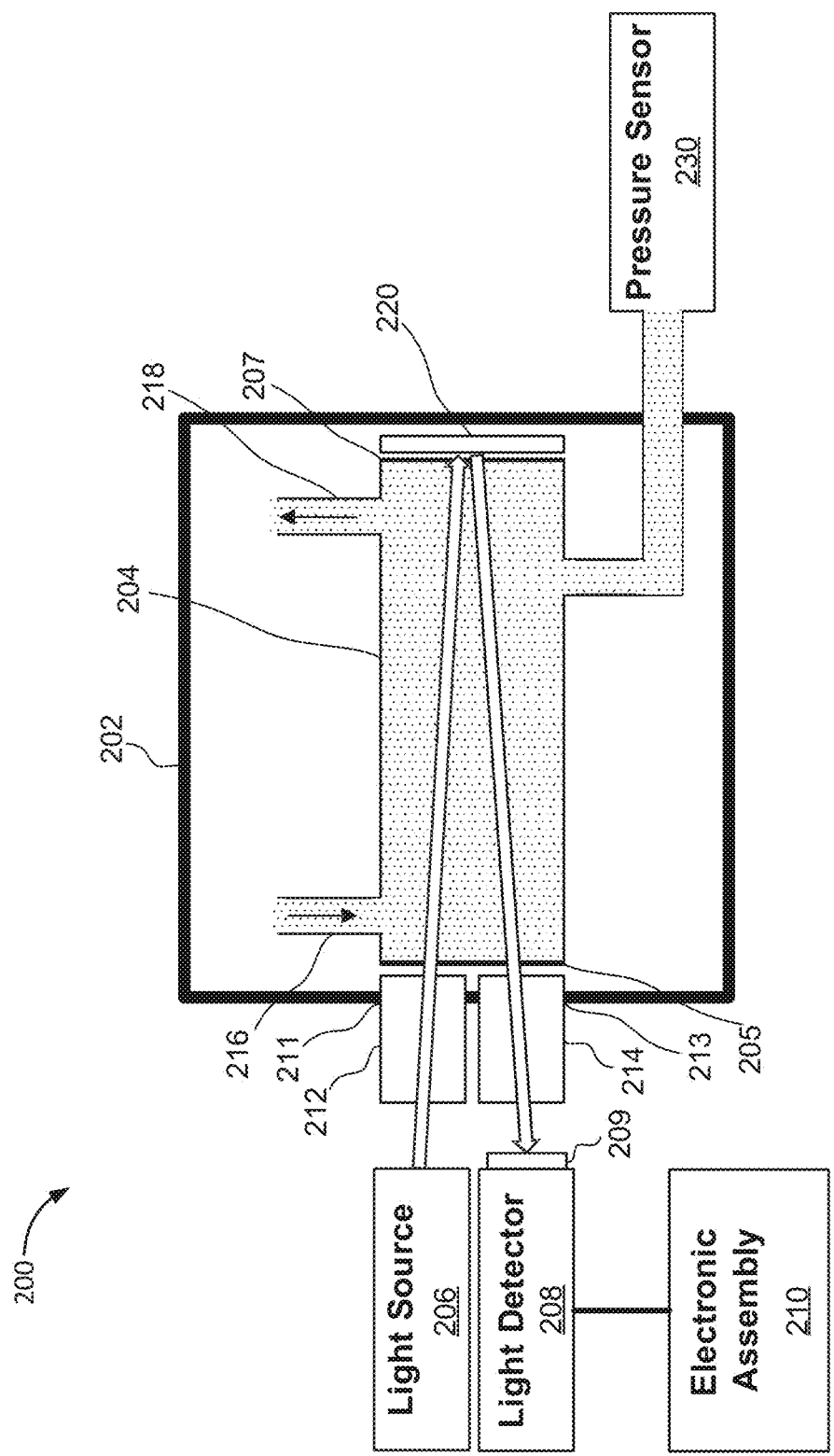
FIG. 2 illustrates a block diagram of an exemplary optical gas concentration measurement apparatus with a two-pass optical configuration, in accordance with one or more embodiments.

FIG. 2 illustrates a block diagram of an exemplary optical gas concentration measurement apparatus 200 with a two-pass optical configuration. The optical gas concentration measurement apparatus 200 may comprise a thermally insulated enclosure 202 having one or more access ports, which may include a first access port 211 and a second access port 213 on the same side of the thermally insulated enclosure. A gas sample cell 204 may be situated within the thermally insulated enclosure 202 and may have a first optical window 205 and a second optical window 207 on two opposing ends of the gas sample cell 204 and one or more gas flow ports, which may include an inlet gas flow port 216 and an outlet gas flow port 218. The first optical window 205 may be proximate both the first access port 211 and the second access port 213.

The gas sample cell 204 may be configured to receive a gas, such as a high temperature chemical process gas, through the inlet gas flow port 216 and expel the gas through the outlet gas flow port 218. A light source 206, a light detector 208, an electronic assembly 210, and a pressure sensor 230 may be positioned outside of the thermally insulated enclosure 202. The light source 206 may be configured to provide light to the gas sample cell 204, such as via the first optical window 205. A first thermally-insulating, light-guiding element 212 may be configured to direct light from the light source 206 to the gas sample cell 204 with a first end adjacent to the light source 206 and a second end adjacent to the first optical window 205 of the gas sample cell 204. A body of the first thermally-insulating, light-guiding element 212 may pass through the first access port 211 of the insulated enclosure 202. A reflective element 220 may be positioned within the thermally insulated enclosure 202 and adjacent to the second optical window 207 of the gas sample cell 204. The reflective element 220 may be configured to reflect light from the first thermally-insulating, light-guiding element 212 towards the first optical window 205.

The light detector 208 may be configured to receive light from the gas sample cell 204, such as via the first optical window 205, and provide information indicative of a chemistry within the gas sample cell 204. The electronic assembly 210 may be configured to receive information from the light detector 208, such as information indicative of a chemistry from the light detector 208 or relating to the amount of light received by the light detector 208, and, in some embodiments, to provide a user-readable output to convey the information to an operator of the optical gas concentration measurement apparatus 200. The pressure sensor 230 may be connected to the gas sample cell 204, such as via tubing, so that the pressure sensor 230 may sample and measure the pressure of the environment within the gas sample cell 204 and send a resulting pressure measurement to the electronic assembly 210. The electronic assembly 210 may be configured to infer a concentration of the gas received by the gas sample cell 204 based on the information received from the light detector 208 and the pressure measurement from the pressure sensor 230. The light source 206, the light detector 208, and the electronic assembly 210 may be thermally isolated from the thermally insulated enclosure 202 and the gas sample cell 204 contained within the thermally insulated enclosure 202.

A second thermally-insulating, light-guiding element 214 may be configured to direct light from the gas sample cell 204 to the light detector 208 and may have a first end adjacent to the light detector 208 and a second end adjacent to the first optical window 205. A body of the second thermally-insulating, light-guiding element 214 may pass through the second access port 213 of the insulated enclosure 202. The first thermally-insulating, light-guiding element 212 and the second thermally-insulating, light-guiding element 214 may each be realized, for example, by a variety of thermally-insulating, light-guiding optical elements that form a single unitary part and may be configured to direct light, such as those comprising light pipes, light guides, hollow light guides with reflective internal walls and windows on each end, optical fibers, or systems of coupled relay lenses that may be constructed of one or more thermally-insulating materials.

For example, the first thermally-insulating, light-guiding element 212 may be a thermally-insulating light guide with a tapered cylindrical shape that may be configured to collimate the light from the light source 206 towards the reflective element 220, and the second thermally-insulating, light-guiding element 214 may be a thermally-insulating light guide with at least one of a tapered rectangular prism or a tapered square prism shape that may be configured to convey light from the gas sample cell 204 to the light detector 208 and distribute the light uniformly across the sensor elements of the light detector 208. Both the first thermally-insulating, light-guiding element 212 and the second thermally-insulating, light-guiding element 214 may, for example, be constructed using a variety of thermally-insulating materials, particularly those with a high working temperature and low bulk absorption, such as $CaF_2$, $MgF_2$, ZnS, sapphire, and aluminum oxynitride (ALON).

The first thermally-insulating, light-guiding element 212, the second thermally-insulating, light-guiding element 214, and the thermally insulated enclosure 202 may be configured to provide enough thermal insulation so as to thermally isolate the gas sample cell 204 from the components of the optical gas concentration measurement apparatus 200 positioned outside of the thermally insulated enclosure 202, such as the light source 206, light detector 208, and electronic assembly 210, which may enable an increase in the lifetime of the optical gas concentration measurement apparatus 200 by limiting the exposure of such components to high temperatures. The thermally insulated enclosure 202 may be constructed of one or more thermally insulating materials and have adequate wall thickness to achieve the thermal isolation mentioned above. Both the first thermally-insulating, light-guiding element 212 and the second thermally-insulating, light-guiding element 214 may have substantial length along an axial dimension, greater than a length along a radial dimension, to provide adequate thermal insulation to achieve the thermal isolation mentioned above and to optically produce the free space optical scheme mentioned above. A gap between both the second end of the first thermally-insulating, light guiding element 212 and the first optical window 205 and the second end of the second thermally-insulating, light guiding element 214 and the first optical window 205 may provide additional thermal insulation. As a result, the first thermally-insulating, light-guiding element 212 may constitute a means for directing light from the light source 206 to the gas sample cell 204 via the one or more optical windows, such as the first optical window 205, while thermally insulating the light source 206 from the gas sample cell 204. Additionally, the second thermally-insulating, light-guiding element 214 may constitute a means for receiving the light from the gas sample cell 204 via the one or more optical windows, such as the first optical window 205, and conveying the light to the light detector 208 while thermally insulating the light detector 208 from the gas sample cell 204.

The thermal isolation provided by the first thermally-insulating, light-guiding element 212, the second thermally-insulating, light-guiding element 214, and the thermally insulated enclosure 202 may also prevent the transfer of heat from the components of the optical gas concentration measurement apparatus 200 positioned outside of the thermally insulated enclosure 202 to the gas sample cell 204 and any gas received by the gas sample cell 204, enabling more precise temperature control of gases received by the gas sample cell 204.

The light source 206 may be configured to provide broad-spectrum, uncollimated light to the first thermally-insulating, light-guiding element 212. For example, the light source 206 may utilize an incandescent light source to provide mid-infrared light to the gas sample cell 204, and the light detector 208 may be configured to receive mid-infrared light. The light from the light source 206 may follow an optical path passing through the first thermally-insulating, light-guiding element 212 and into the gas sample cell 204 via the first optical window 205. The first thermally-insulating, light-guiding element 212 may direct and collimate the light using its shape, focusing the light into a narrower beam towards the reflective element 220 and away from the gas sample cell 204 walls to create a free space optical scheme. As a result, the gas sample cell 204 walls do not participate significantly in light propagation and their contamination does not impact gas detectivity, enabling for an increased lifetime of the optical gas concentration measurement apparatus 200.

The reflective element 220 may be configured to direct the optical path of the light within the gas sample cell 204 and may be positioned on the exterior of the gas sample cell 204, enabling an increased lifespan of the reflective element 220 by eliminating its exposure to the gas sample cell 204 environment and any potential contaminants contained therein. For example, the reflective element 220 may receive light from the light source 206 via the gas sample cell 204 and direct the optical path of the light back through the gas sample cell 204 and towards the light detector 208 while maintaining the free optical space scheme by avoiding directing light towards the gas sample cell 204 walls. The reflective element may be realized, for example, by at least one of a mirror, a re-imaging retroreflective array with fixed angular offset, and any other optically reflective element known in the art. The reflective element 220 may enable optical access to the gas sample cell for the light source 206 and light detector 208 via a single side of the thermally insulated enclosure 202, which may be advantageous in applications with space constraints. Additionally, the two-pass configuration enabled by the reflective element 220 may aid in accurately detecting low concentration gasses or gasses that absorb less light.

Both times the light passes through the gas sample cell 204, the gas received by the gas sample cell 204 may absorb a portion of the light. The light may then pass through the second thermally-insulating, light-guiding element 214 via the first optical window 205 and be transmitted to the light detector 208. An optical filter 209 may be coupled to the light detector 208 and be configured to filter the light transmitted from the gas sample cell 204 to the light detector 208, enabling the light detector 208 to be tuned to detect specific gases. For example, the optical filter 209 may be a band-pass filter tuned to allow a specific wavelength of light, such as 3-5 microns, associated with a specific gas to pass through to the light detector 208. The light detector 208 may emit a signal to the electronic assembly 210 based on the amount of light detected.

The gas sample cell 204 may have a variety of shapes and volumes depending on the application. For example, the gas sample cell 204 may have a cylindrical shape optimized for maximum transmission of light. In another example, the gas sample cell 204 may have a rectangular prism shape or a cylindrical shape with an oval cross-section, which may be particularly useful in applications with specific space constraints; however, such geometries may vignette a portion of the light transferred through the gas sample cell 204, decreasing light transmission.

In other embodiments, the light detector 208 may be a large area light detector and the second thermally-insulating, light-guiding element 214 may be replaced by a thermally-insulating optical element that does not provide light-guiding functionality.

In other embodiments, it is contemplated that the light source 206 may be a laser that follows a similar two-pass optical path to the broad-spectrum light. The wavelength of the laser may be chosen based on the type of gas to be detected. Optionally, the optical filter 209 may be removed in such embodiments since the laser light may not need filtering. However, using only a specific wavelength of light may limit the number of different gas types that can be detected by the light detector 208.

Figure 3:
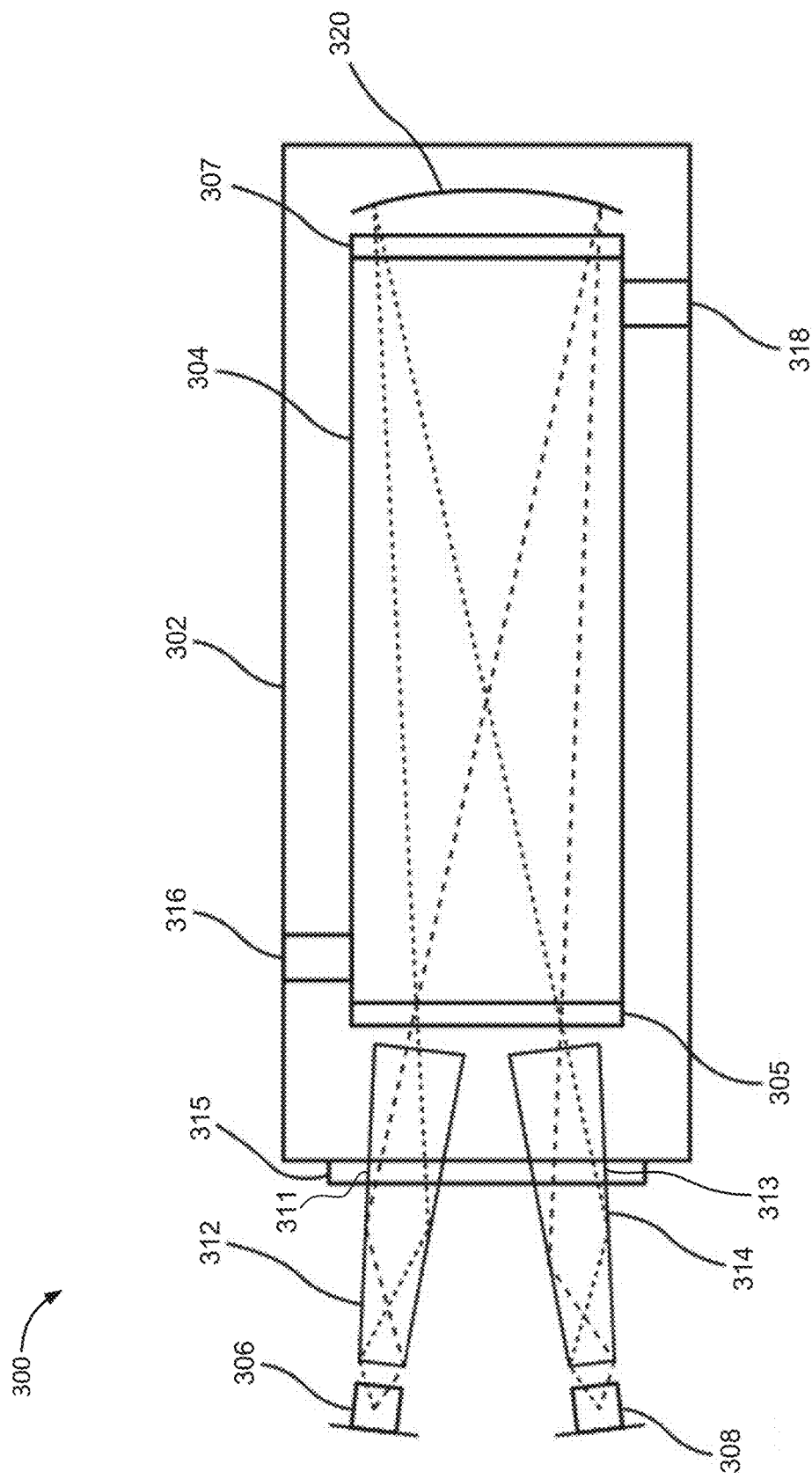
FIG. 3 illustrates a cross-sectional view of an exemplary optical gas concentration measurement apparatus with a two-pass optical configuration, in accordance with one or more embodiments.

FIG. 3 illustrates a cross-sectional view of an exemplary optical gas concentration measurement apparatus 300 with a two-pass optical configuration, which may be a realization of the optical gas concentration measurement apparatus 200 depicted in the block diagram of FIG. 2, wherein the thermally-insulating, light-guiding elements are realized by thermally-insulating light guides. The optical gas concentration measurement apparatus 300 may comprise a thermally insulated enclosure 302 having one or more access ports, which may include a first access port 311 and a second access port 313 seated within an insulated mounting flange 315 on one side of the thermally insulated enclosure 302. A gas sample cell 304 may be situated within the thermally insulated enclosure 302 and may have a first optical window 305 and a second optical window 307 on two opposing ends of the gas sample cell 304 and one or more gas flow ports, which may include an inlet gas flow port 316 and an outlet gas flow port 318. The first optical window 305 may be proximate both the first access port 311 and the second access port 313.

Figure 6:
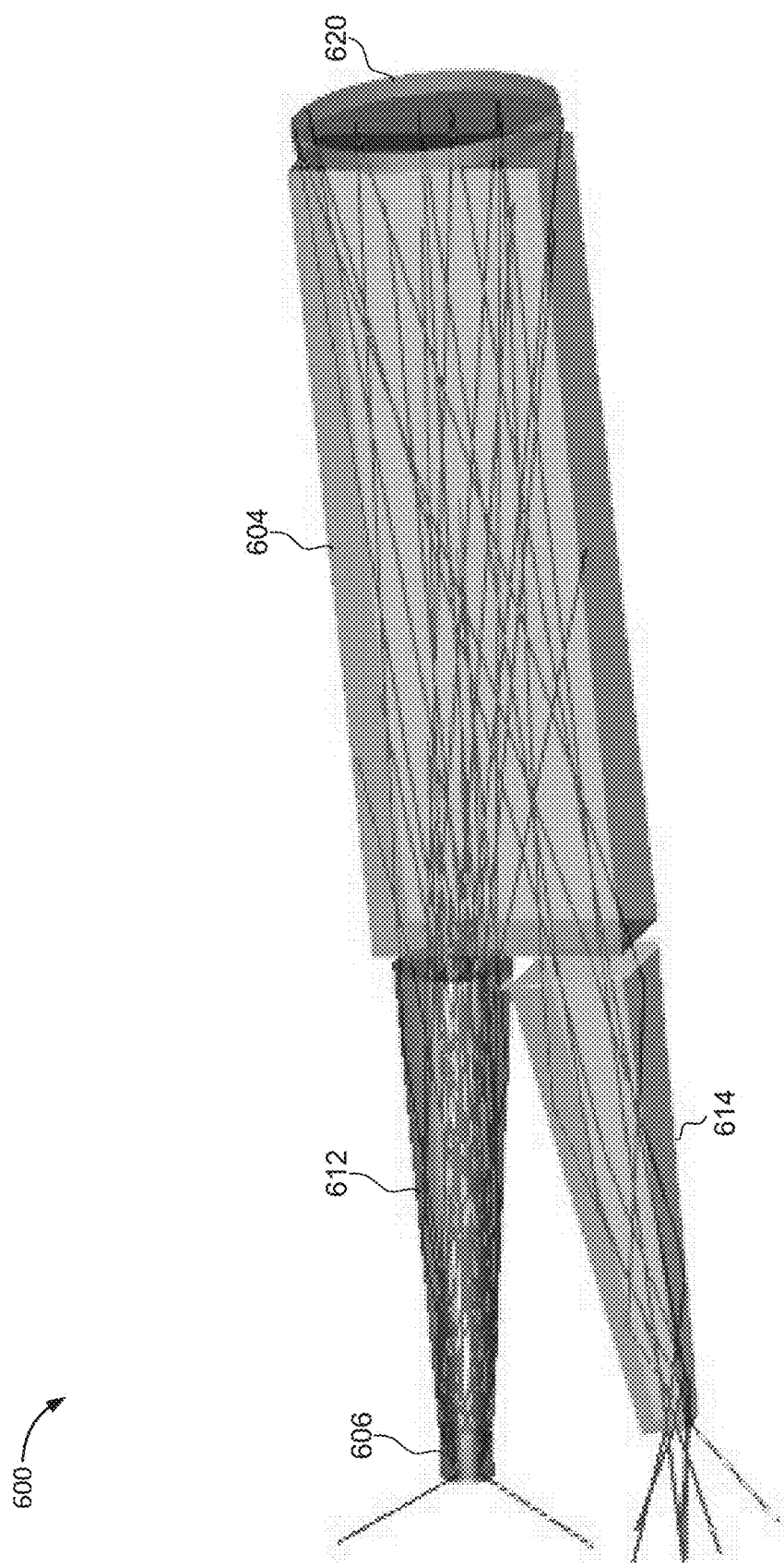
FIG. 6 illustrates a computer-generated ray tracing model of an exemplary optical gas concentration measurement apparatus with a two-pass optical configuration and a gas sample cell with a rectangular prism shape, in accordance with one or more embodiments.

The gas sample cell 304 may be comprised of a hollow elongated volume with a cylindrical shape and may be configured to receive a gas, such as a high temperature chemical process gas, through the inlet gas flow port 316 and expel the gas through the outlet gas flow port 318; however, in other embodiments, the gas sample cell 304 may have a rectangular prism shape as shown in FIG. 6. The walls of the gas sample cell 304, the first optical window 305, and the second optical window 307 may provide a sealed space for the gas, enabling the protection of other optical gas concentration measurement apparatus 300 components from contamination by the gas. A light source 306, a light detector 308, and an electronic assembly (not shown) may be positioned outside of and thermally isolated from the thermally insulated enclosure 302 and the gas sample cell 304 contained within the thermally insulated enclosure 302.

The light source 306 may be configured to provide light to the gas sample cell 304 via the first optical window 305. A first thermally-insulating light guide 312 may be configured to direct light from the light source 306 to the gas sample cell 304 with a first end adjacent to the light source 306 and a second end adjacent to the first optical window 305 of the gas sample cell 304. A body of the first thermally-insulating light guide 312 may pass through the first access port 311 of the insulated enclosure 302. A reflective element 320 may be positioned within the thermally insulated enclosure 302 and adjacent to the second optical window 307 of the gas sample cell 304. The reflective element 320 may be configured to reflect light from the first thermally-insulating light guide 312 towards the first optical window 305. The light detector 308 may be configured to receive light from the gas sample cell 304 via the first optical window 305. The electronic assembly 310 may be configured to receive information from the light detector 308, such as information relating to the amount of light received by the light detector 308. The electronic assembly 310 may be configured to infer a concentration of the gas received by the gas sample cell 304 based on the information received from the light detector 308.

Figure 4:
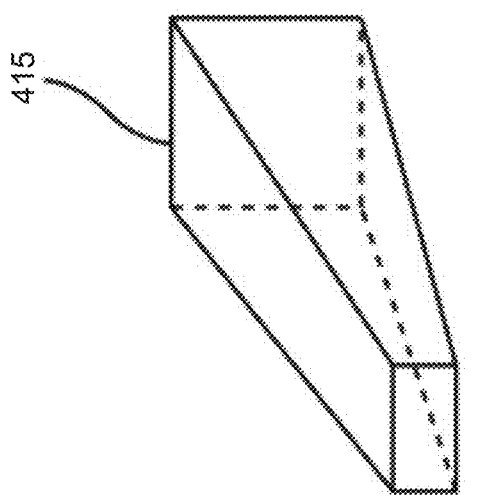
FIG. 4 illustrates thermally-insulating light guides of various geometries, in accordance with one or more embodiments.
Figure 4:
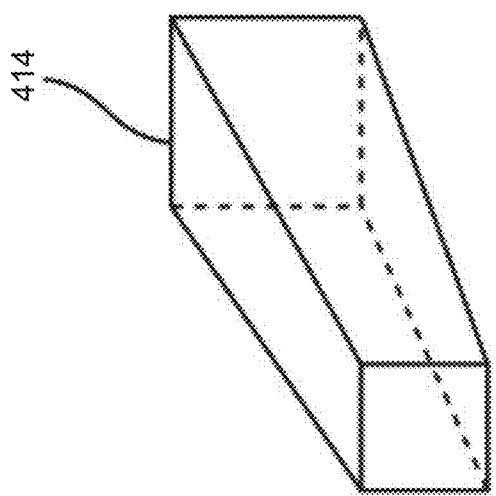
Figure 4:
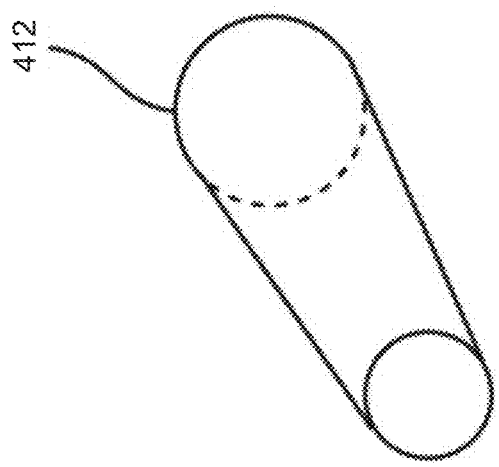

A second thermally-insulating light guide 314 may be configured to direct light from the gas sample cell 304 to the light detector 308 and may have a first end adjacent to the light detector 308 and a second end adjacent to the first optical window 305. A body of the second thermally-insulating light guide 314 may pass through the second access port 313 of the insulated enclosure 302. The first thermally-insulating light guide 312 and the second thermally-insulating light guide 314 may each be a unitary part constructed of a solid thermally-insulating material that may transmit light, such as $CaF_2$, $MgF_2$, ZnS, sapphire, or ALON, which may be polished improve light transmission. The first thermally-insulating light guide 312 may have a tapered cylindrical shape that may be configured to collimate the light from the light source 306 towards the reflective element 320, and the second thermally-insulating light guide 314 may also have a tapered cylindrical shape that may be configured to convey light from the gas sample cell 304 to the light detector 308 and concentrate the light onto sensor elements of the light detector 308; however, in other embodiments, the second thermally-insulating light guide 314 may have at least one of a tapered rectangular prism or a tapered square prism shape as depicted in FIG. 4.

The first thermally-insulating light guide 312, the second thermally-insulating light guide 314, and the thermally insulated enclosure 302 may be configured to provide adequate thermal insulation to thermally isolate the interior of the thermally insulated enclosure 302 and the gas sample cell 304 from the components of the optical gas concentration measurement apparatus 300 positioned outside of the thermally insulated enclosure 302, such as the light source 306, light detector 308, and electronic assembly, which may enable an increase in the lifetime of the optical gas concentration measurement apparatus 300 by limiting the exposure of such components to high temperatures.

The thermally insulated enclosure 302 may be constructed of one or more thermally insulating materials and have adequate wall thickness to achieve the thermal isolation mentioned above. Both the first thermally-insulating light guide 312 and the second thermally-insulating light guide 314 may have substantial length along an axial dimension, greater than a length along a radial dimension, to provide adequate thermal insulation to achieve the thermal isolation mentioned above and to optically produce the free space optical scheme mentioned above. A gap between the first optical window 305 and both the second end of the first thermally-insulating light guide 312 and the second end of the second thermally-insulating light guide 314 may provide additional thermal insulation. As a result, the first thermally-insulating light guide 312 may constitute a means for directing light from the light source 306 to the gas sample cell 304 via the one or more optical windows, such as the first optical window 305, while thermally insulating the light source 306 from the gas sample cell 304. Additionally, the second thermally-insulating light guide 314 may constitute a means for receiving the light from the gas sample cell 304 via the one or more optical windows, such as the first optical window 305, and conveying the light to the light detector 308 while thermally insulating the light detector 308 from the gas sample cell 304.

The thermal isolation provided by the first thermally-insulating light guide 312, the second thermally-insulating light guide 314, and the thermally insulated enclosure 302 may also prevent the transfer of heat from the components of the optical gas concentration measurement apparatus 300 positioned outside of the thermally insulated enclosure 302 to the gas sample cell 304 and any gas received by the gas sample cell 304, enabling more precise temperature control of gases received by the gas sample cell 304 by limiting the effect of extraneous, uncontrolled heat sources.

The light source 306 may be configured to provide broad-spectrum, uncollimated light to the first thermally-insulating light guide 312. For example, the light source 306 may utilize an incandescent light source to provide mid-infrared light to the gas sample cell 304, and the light detector 308 may be configured to receive mid-infrared light. The light from the light source 306 may follow an optical path, as demonstrated by the dotted lines, passing through the first thermally-insulating light guide 312 and into the gas sample cell 304 via the first optical window 305. The first thermally-insulating light guide 312 may direct and collimate the light using its shape, focusing the light in a narrower beam towards the reflective element 320 and away from the gas sample cell 304 walls to create a free space optical scheme. The reflective element 320 may be a concave mirror with a coating, such as gold or aluminum, configured to direct the optical path of the light within the gas sample cell 304 and may be positioned on the exterior of the gas sample cell 304, enabling an increased lifespan of the reflective element 320 by eliminating its exposure to the gas sample cell 304 environment and any potential contaminants contained therein. For example, the reflective element 320 may receive light from the light source 306 via the gas sample cell 304 and direct the optical path of the light back through the gas sample cell 304 and towards the light detector 308. The reflective element 320 may enable optical access to the gas sample cell for the light source 306 and light detector 308 via a single side of the thermally insulated enclosure. Additionally, the two-pass configuration enabled by the reflective element 320 may aid in accurately detecting low concentration gasses or gasses that absorb less light.

The light reflected by the reflective element 320 through the gas sample cell 304 may then pass through the second thermally-insulating light guide 314 via the first optical window 305 and be transmitted to the light detector 308. The light detector 308 may be realized, for example, by a thermopile, pyroelectric detector, or other light detector known in the art. An optical filter 309 may be coupled to the light detector 308 and be configured to filter the light transmitted from the gas sample cell 304 to the light detector 308, enabling the light detector 308 to be tuned to detect specific gases. For example, the optical filter 309 may be a band-pass filter tuned to allow a specific wavelength of light, such as 3-5 microns, associated with a specific gas to pass through to the light detector 308. The light detector 308 may emit a signal to the electronic assembly 310 based on the amount of light detected.

FIG. 4 illustrates thermally-insulating light guides of various geometries. The overall geometry, or shape, of a thermally-insulating light guide may be optimized for its specific application. For example, a tapered cylindrical thermally-insulating light guide 412 may be used to collimate light from a light source into a narrower beam, such as in the FIG. 2 and FIG. 3 exemplary embodiments; however, a tapered cylindrical thermally-insulating light guide 412 may be sub-optimal when used to concentrate light onto certain sensor elements of a light detector. For example, some light detectors may have a dual or quad sensor element arrangement, such as two sensor elements arranged side-by-side or four sensor elements arranged in a square respectively, and a tapered cylindrical thermally-insulating light guide 412 may concentrate light into a circular area, producing an nonuniform distribution of light across such sensor elements.

Instead, a tapered square prism thermally-insulating light guide 414 may be used for light detectors with a square, quad sensor element arrangement, and a tapered rectangular prism thermally-insulating light guide 415 may be used for light detectors with a side-by-side, dual sensor element arrangement. Both the tapered square prism thermally-insulating light guide 414 and the tapered rectangular prism thermally-insulating light guide 415 may exhibit a homogenizing property of uniformly distributing light over the sensor elements when each is used to concentrate light onto the appropriate sensor element arrangement, quad and dual respectively, enabling greater accuracy and consistency in light detector measurements. Each of the tapered square prism thermally-insulating light guide 414 and the tapered rectangular prism thermally-insulating light guide 415 may be used, for example, in accordance with a sensor element arrangement of a particular light detector to realize the second thermally-insulating, light-guiding element 214 of FIG. 2, to replace the second thermally-insulating light guide 314 of FIG. 3, or to more generally, in some embodiments, serve as a means for receiving light from a gas sample cell via one or more optical windows of the gas sample cell and for conveying the light to a light detector while thermally insulating the light detector from the gas sample cell.

Figure 5:
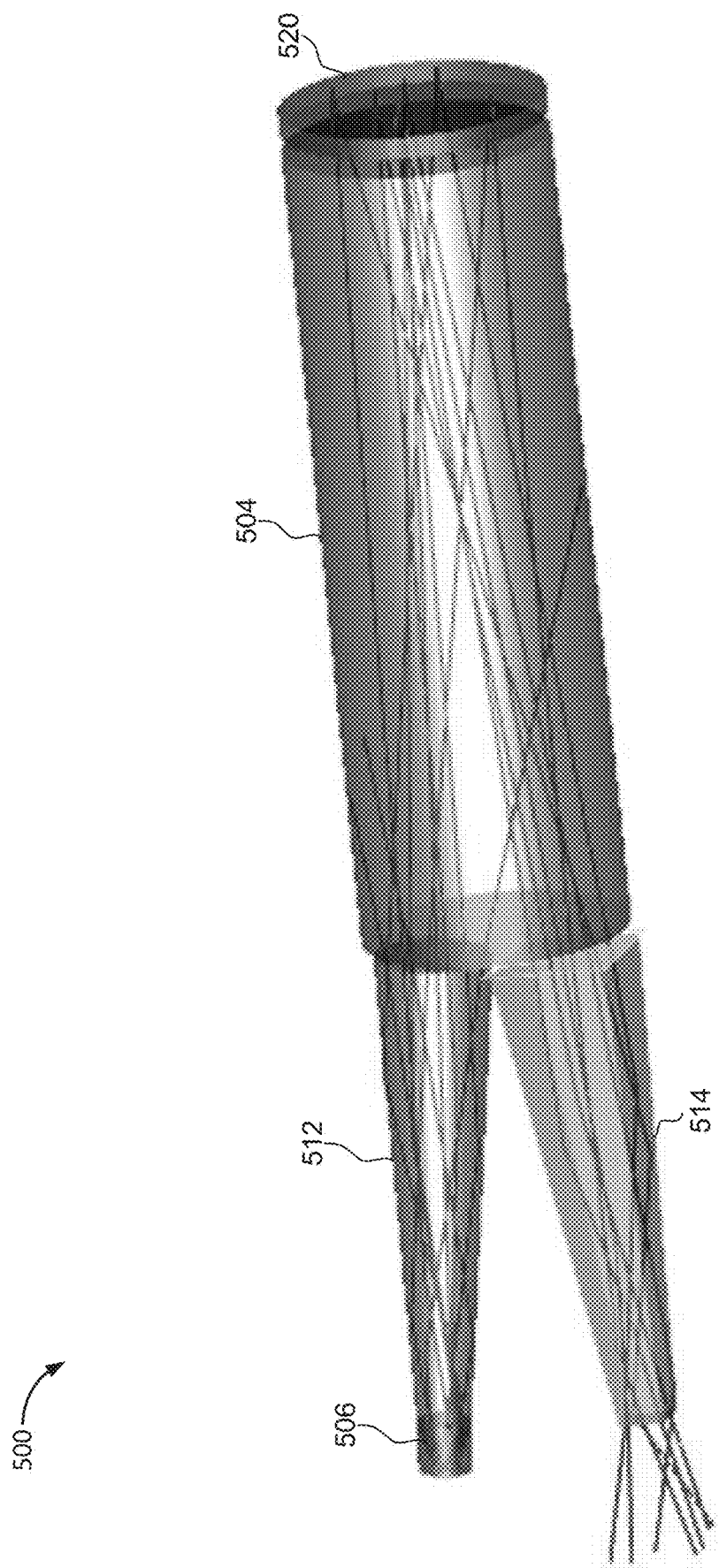
FIG. 5 illustrates a computer-generated ray tracing model of an exemplary optical gas concentration measurement apparatus with a two-pass optical configuration, in accordance with one or more embodiments.

FIG. 5 illustrates a computer-generated ray tracing model of an exemplary optical gas concentration measurement apparatus 500 with a two-pass optical configuration. Light, shown as light rays represented by lines, is emitted from a light source 506 through a first thermally-insulating light guide 512, which utilizes internal reflections and a tapered cylindrical shape to collimate the light into a narrow beam directed through a cylindrical gas sample cell 504 and towards a reflective element 520. The light is then reflected by the reflective element 520 back through the gas sample cell 504 and towards a second thermally-insulating light guide 514 with a tapered square prism shape that concentrates the light. The majority of the light from the light source 506 passes through the gas sample cell 504 in a free space optical scheme and reaches the end of the second thermally-insulating light guide 514 where a light detector would be positioned to measure the transmitted light.

FIG. 6 illustrates a computer-generated ray tracing model of an exemplary optical gas concentration measurement apparatus 600 with a two-pass optical configuration and a gas sample cell 604 with a rectangular prism shape. Light, shown as light rays represented by lines, is emitted from a light source 606 through a first thermally-insulating light guide 612, which utilizes internal reflections and a tapered cylindrical shape to collimate the light into a narrow beam directed through a gas sample cell 604 with a rectangular prism shape and towards a reflective element 620. The light is then reflected by the reflective element 620 back through the gas sample cell 604 and towards a second thermally-insulating light guide 614 with a tapered square prism shape that concentrates the light. The light from the light source 606 passes through the gas sample cell 604 in a free space optical scheme and reaches the end of the second thermally-insulating light guide 614 where a light detector would be positioned to measure the transmitted light; however, a smaller proportion of the light from the light source 606 reaches the end of the second thermally-insulating light guide 614 than in the FIG. 5 embodiment. This reduction in light transmission is caused by the rectangular prism shape of the gas sample cell 604 vignetting a portion of the transmitted light, as shown by the light rays that hit the walls of the gas sample cell 604; however, the volume reduction of such a rectangular prism shape may enable the optical gas concentration measurement apparatus 600 to meet the needs of certain applications that may value space over maximizing light transmission.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An optical gas concentration measurement apparatus comprising:
  a thermally insulated enclosure having one or more access ports;
  a gas sample cell situated within the thermally insulated enclosure, the gas sample cell comprising one or more optical windows and one or more gas flow ports;
  a light source outside of the thermally insulated enclosure configured to provide light to the gas sample cell;
  a first thermally-insulating, light-guiding element passing through a first access port of the thermally insulated enclosure, the first thermally-insulating, light-guiding element configured to direct light from the light source to the gas sample cell via the one or more optical windows;
  a light detector outside of the thermally insulated enclosure configured to receive light from the gas sample cell via the one or more optical windows;
  a second thermally-insulating, light-guiding element passing through a second access port of the thermally insulated enclosure, the second thermally-insulating, light-guiding element configured to direct light from the gas sample cell to the light detector, wherein the second thermally-insulating, light-guiding element has at least one of a tapered rectangular prism or a tapered square prism shape; and an electronic assembly outside of the thermally insulated enclosure configured to receive information from the light detector.

2. The optical gas concentration measurement apparatus of claim 1, further comprising:

one or more reflective elements configured to direct an optical path of the light within the gas sample cell.

3. The optical gas concentration measurement apparatus of claim 1, wherein the first thermally-insulating, light-guiding element has a tapered cylindrical shape and is configured to collimate the light from the light source.

4. An optical gas concentration measurement apparatus comprising:

a thermally insulated enclosure having one or more access ports;

a gas sample cell situated within the thermally insulated enclosure, the gas sample cell comprising one or more optical windows and one or more gas flow ports;

a light source outside of the thermally insulated enclosure configured to provide light to the gas sample cell;

means for directing light from the light source to the gas sample cell via the one or more optical windows while thermally insulating the light source from the gas sample cell;

a light detector outside of the thermally insulated enclosure configured to receive light from the gas sample cell and provide information indicative of a chemistry within the gas sample cell;

means for receiving the light from the gas sample cell via the one or more optical windows and conveying the light to the light detector while thermally insulating the light detector from the gas sample cell, wherein the means for receiving comprises at least one of a tapered rectangular prism or a tapered square prism shape; and an electronic assembly outside of the thermally insulated enclosure configured to receive the information indicative of a chemistry from the light detector and provide a user-readable output to convey the information to an operator of the measurement apparatus.

5. The optical gas concentration measurement apparatus of claim 4 comprising:

one or more reflective elements configured to direct an optical path of the light within the gas sample cell.

6. The optical gas concentration measurement apparatus of claim 4, wherein the means for directing comprises a tapered cylindrical shape and is configured to collimate the light from the light source.

* * * * *